United States Patent
Kjeldsen et al.

(10) Patent No.: US 7,402,565 B2
(45) Date of Patent: Jul. 22, 2008

(54) PROCESSES FOR MAKING ACYLATED INSULIN

(75) Inventors: Thomas Børglum Kjeldsen, Virum (DK); Jan Markussen, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/418,004

(22) Filed: May 3, 2006

(65) Prior Publication Data

US 2006/0264606 A1    Nov. 23, 2006

Related U.S. Application Data

(63) Continuation of application No. PCT/DK2004/000782, filed on Nov. 11, 2004.

(60) Provisional application No. 60/523,389, filed on Nov. 19, 2003.

(30) Foreign Application Priority Data

Nov. 14, 2003  (DK) ................. 2003 01692

(51) Int. Cl.
*A61K 38/28* (2006.01)
*A61K 38/00* (2006.01)
*C07K 14/62* (2006.01)

(52) U.S. Cl. ............... 514/3; 514/2; 530/300; 530/303

(58) Field of Classification Search ........... None
See application file for complete search history.

(56) References Cited

U.S. PATENT DOCUMENTS

| | | | |
|---|---|---|---|
| 5,646,242 A | 7/1997 | Baker et al. | |
| 5,693,609 A | 12/1997 | Baker et al. | |
| 5,750,497 A | 5/1998 | Havelund et al. | |
| 5,905,140 A | 5/1999 | Hansen | |
| 5,922,675 A | 7/1999 | Baker et al. | |
| 6,011,007 A | 1/2000 | Havelund et al. | |
| RE37,971 E | 1/2003 | Baker et al. | |

FOREIGN PATENT DOCUMENTS

| | | |
|---|---|---|
| EP | 163529 | 5/1985 |
| EP | 792290 | 9/1994 |
| EP | 1132404 | 9/1994 |
| EP | 712862 | 11/1995 |
| EP | 894095 | 2/1997 |
| WO | 96/29344 | 3/1996 |
| WO | 98/02460 | 7/1997 |
| WO | WO 02/079250 | * 10/2002 |
| WO | 03/010186 | 2/2003 |

OTHER PUBLICATIONS

Kjeldsen, T—Appl Microbiol Biotechnol—2000—vol. 54—pp. 277-286.
Kjeldsen, T et al—Prot Expres Purif—1998—vol. 14—pp. 309-316.
Kjeldsen, T et al—Gene—1996—vol. 170—pp. 107-110.

* cited by examiner

*Primary Examiner*—Anish Gupta
*Assistant Examiner*—Julie Ha
(74) *Attorney, Agent, or Firm*—Shelby J. Walker

(57) ABSTRACT

A method is provided which allows high yields of acylated insulin. The method comprises expressing a singe-chain insulin precursor, preferably in yeast, cleaving the single-chain insulin precursor with a suitable protease which will open the peptide bond between the C-terminal amino group in the B-chain and a connecting peptide connecting the B chain with the A-chain, acylating the two-chain insulin intermediate in the $\epsilon$-amino group in $Lys^{B29}$ and subjecting the acylated two-chain insulin intermediate to a proteolytic enzyme which will cleave of the N-terminal extension on the B- and A-chains on the precursor molecule.

16 Claims, 1 Drawing Sheet

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial
<220> FEATURE:
```

```
<223> OTHER INFORMATION: Synthetic

<400> SEQUENCE: 1

Asp Asp Gly Asp Pro Arg
1               5

<210> SEQ ID NO 2
<211> LENGTH: 6
<212> TYPE: PRT
<213> ORGANISM: Artificial
<220> FEATURE:
<223> OTHER INFORMATION: Synthetic

<400> SEQUENCE: 2

Glu Glu Gly Glu Pro Arg
1               5

<210> SEQ ID NO 3
<211> LENGTH: 6
<212> TYPE: PRT
<213> ORGANISM: Artificial
<220> FEATURE:
<223> OTHER INFORMATION: Synthetic

<400> SEQUENCE: 3

Asp Asp Gly Asp Gly Arg
1               5

<210> SEQ ID NO 4
<211> LENGTH: 6
<212> TYPE: PRT
<213> ORGANISM: Artificial
<220> FEATURE:
<223> OTHER INFORMATION: Synthetic

<400> SEQUENCE: 4

Glu Glu Gly Glu Gly Arg
1               5
```

PROCESSES FOR MAKING ACYLATED INSULIN

CROSS REFERENCE TO RELATED APPLICATIONS

This application is a continuation of International Application serial no. PCT/DK2004/000782 filed Nov. 11, 2004 and claims priority from Danish Application serial no. PA 2003 01692 filed Nov. 14, 2003 and of U.S. provisional application Ser. No. 60/523,389 filed on Nov. 19, 2003.

FIELD OF THE INVENTION

The present invention is related to processes for making acylated insulin or insulin analogues, to the intermediates used in such processes and to the acylated insulins and insulin analogues produced by such processes.

BACKGROUND OF THE INVENTION

Many diabetic patients are treated with multiple daily insulin injections in a regimen comprising one or two daily injections of a protracted insulin to cover the basal requirement supplemented by bolus injections of a rapid acting insulin to cover the requirement related to meals.

A class of compounds suitable for this task is insulin derivatives in which the ε-amino group in the lysine residue in position 29 of the B-chain is acylated with a hydrophobic moiety. Such compounds are disclosed in EP patents 792,290 and 894,095 and in U.S. Pat. Nos. 5,693,609, 5,646,242, 5,922,675, 5,750,497 and 6,011,007.

Human insulin and closely related insulins have three primary amino groups in the molecule namely the α-amino groups of $Gly^{A1}$ and $Phe^{B1}$, respectively, and the ε-amino group of $Lys^{B29}$. N-Acylation of unprotected insulin may—depending on the conditions—lead to a complex mixture of mono-, di- and even triacylated products. However, although a certain preference for acylation of a specific position can often be observed the preference is not always sufficiently pronounced to make such direct acylation useful as a method of producing monoacylated insulins since the formation of the desired monoacylated product may be accompanied by the formation of considerable amounts of closely related unwanted by-products such as di- and tri-acylated insulins. When such unwanted are formed, this happens at the expense of the desired product and may lead to problems in the purification of the desired product.

Acylation of only one or two specific amino groups in the insulin molecule can be achieved if a suitably protected intermediate is available. A suitable intermediate can be an insulin molecule in which the amino group(s) not to be acylated is (are) blocked with a protection group which can be removed selectively after the acylation has been performed. Such a protected intermediate can be an insulin molecule in which one or two protection groups have been introduced posttranslationally in a specific way. For economic reasons, it is however very attractive to avoid the use of specific protection groups if possible.

Selective acylation at pH above 9 by use of an activated ester of a fatty acid of, in particular, a free ε-amino group in either position B29 or in position B28 is disclosed on U.S. Pat. No. RE 37971. U.S. Pat. No. 5,905,140 discloses selective acylation of a free ε-amino group in insulin by used of an activated amide.

The present invention is related to a process for obtaining high yields of insulin or an insulin analogue being acylated in an ε-amino group, in particular the ε-amino group in $Lys^{B29}$.

SUMMARY OF THE INVENTION

In one aspect the present invention is related to a method for making acylated insulin or an acylated insulin analogue wherein a two-chain insulin intermediate with N-terminal protecting peptide sequences attached to the B1 N-terminal amino acid group and to the A1 N-terminal amino acid group is acylated in a free ε-amino group whereupon the protecting peptide sequences are cleaved off and the desired acylated insulin is isolated.

The claimed method may comprise the following steps:
a) acylating an insulin intermediate having the formula

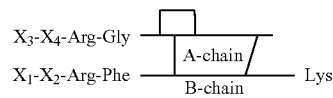

in which $X_1$ is Asp or Glu, $X_2$ is a peptide sequence with 1-10 amino acid residues except Cys, Lys and Arg or is a peptide bond, $X_3$ is Asp or Glu, and $X_4$ is a peptide sequence with 1-10 amino acid residues except Cys, Lys and Arg or is a peptide bond, B-chain is the B-chain of human insulin or an analogue thereof, and A-chain is the A-chain of human insulin or an analogue thereof, at the C-terminal lysine amino group in the B-chain, and b) cleaving the peptide bond between Arg and B1 and between Arg and A1 in the acylated insulin intermediate by trypsin or a trypsin like protease to produce an acylated insulin or insulin analogue.

In one embodiment of the present invention the two-chain insulin intermediate used in step a) may be produced by cleavage of a single-chain insulin precursor having the formula

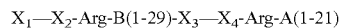

in which $X_1$ is Asp or Glu, $X_2$ is a peptide sequence with 1-10 amino acid residues except Cys, Lys and Arg or is a peptide bond, $X_3$ is Asp or Glu, and $X_4$ is a peptide sequence with 1-10 amino acid residues except Cys, Lys and Arg or is a peptide bond, B(1-29) is the B-chain of human insulin lacking the B30 amino acid residue or an analogue thereof, and A(1-21) is the A-chain of human insulin or an analogue thereof, with a lysine specific protease that cleaves the peptide bond between $Lys^{B29}$ and $X_3$.

In a further embodiment the method will comprise a step of isolating the acylated insulin or insulin analogue produced in b).

In another aspect the present invention is related to a method for making an acylated insulin or insulin analogue comprising i) cleaving a single-chain insulin precursor having the formula

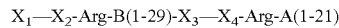

in which $X_1$ is Asp or Glu, $X_2$ is a peptide sequence with 1-10 amino acid residues except Cys, Lys and Arg or is a peptide bond, $X_3$ is Asp or Glu, and $X_4$ is a peptide sequence with 1-10 amino acid residues except Cys, Lys and Arg or is a peptide bond, B(1-29) is the B-chain of human insulin lacking the B30 amino acid residue or an analogue thereof, and A(1-21) is the A-chain of human insulin or an analogue thereof, with a lysine specific protease whereby the peptide bond between $Lys^{B29}$ and $X_3$ is cleaved, ii) acylating the opened two-chain insulin intermediate in the ε-lysine amino group in position B29 with a fatty acid,
iii) cleaving peptide bond between Arg and B1 and between Arg and A1 in the acylated insulin intermediate by trypsin or a trypsin like protease, and
iv) isolating the acylated insulin or insulin analogue.

In a still further aspect the present invention is related to a method comprising the following steps:
i) cleaving a single-chain insulin precursor having the formula $$X_1—X_2\text{-Arg-B}(1\text{-}29)\text{-}X_3—X_4\text{-Arg-A}(1\text{-}21)$$

in which $X_1$ is Asp or Glu, $X_2$ is a peptide sequence with 1-10 amino acid residues except Cys, Lys and Arg or is a peptide bond, $X_3$ is Asp or Glu, and $X_4$ is a peptide sequence with 1-10 amino acid residues except Cys, Lys and Arg or is a peptide bond, with a lysine specific protease whereby the peptide bond between B29 and $X_3$ is cleaved and a two-chain insulin intermediate is formed,
ii) acylating the two-chain insulin precursor in the E-lysine amino group in position B29 with a fatty acid,
iii) cleaving peptide bond between Arg and B1 and between Arg and A1 in the acylated precursor by trypsin or a trypsin like protease, and
iv) isolating the acylated insulin.

The lysine specific protease used in step i) can be any suitable protease which is capable of cleaving at the lysine residue without cleaving at an arginine residue. In this step the insulin precursor is only cleaved at the lysine residue in B29. In one embodiment the lysine specific protease is *Achromobacter lyticus* protease.

The acylation agent in step a) or ii) is used in a moderate excess of up to about 5 equivalents and in one embodiment it is used in an amount of from 1 to 5 equivalents. In a further embodiment the acylation agent is used in an amount of from 1 to 3 equivalents.

The acylation agent can be any suitable acylation agent capable of introducing a fatty acyl group in the desired position. Non limiting examples of acylation agents are activated esters or amides of fatty acids. Further suitable acylation agents are anhydrides, halides or azoles of fatty acids.

In one embodiment of the present invention the activated fatty acid ester is an N-hydroxysuccinimide ester of a fatty acid.

The acylation step a) or ii) is conducted at basic pH and in a polar solvent. The pH in step b) may be selected from the range of about 9 to about 10.5. In one embodiment the pH is between 9.2 and 10.5 and in another embodiment the pH is between 9.5 and 10.3 or between 9.7 and 10.3. In a still further embodiment the pH in step a) or i) is between about 9,3 and about 9,9.

The fatty acid may be a linear or branched saturated or unsaturated carboxylic acid having at least 2 carbon atoms. In one embodiment of the present invention the fatty acid has from 6-30; 6-24; 6-18; 6-14; 10-30; and 10-24.

In one embodiment the fatty acid has from 6-18; 10-18 C-atoms or from 10-14 C-atoms.

According to a further embodiment the fatty is selected from the group consisting of capric acid, lauric acid, tetradecanoic acid (myristic acid), pentadecanoic acid, palmitic acid, heptadecanoic acid, stearic acid, dodecanoic acid, tridecanoic acid, and tetradecanoic acid.

The solvent in step a) or ii) can be a mixture of water and a water mixable organic solvent selected from the group consisting of NMP, DMF, DMAC, acetonitrile, tetrahydrofurane, dioxan, methanol, ethanol isopropanol and tert.-butanol.

The content of organic solvent may be between 25 and 75% (v/v), between 33 and 67%, or may be about 50%.

The length of the peptide sequence $X_2$ and $X_4$ may vary between 1 and 10 amino acid residues. In one embodiment $X_2$ and $X_4$ are from 2-8, from 2-6, from 2-5, from 2-4 or from 2-3 amino acid residues long and $X_2$ and $X_4$ may each by 1, 2, 3, 4 5, 6, 7, 8, 9 or 10 amino acids long.

In one embodiment $X_2$ will comprise at least one Gly to enhance the rate of cleavage by trypsin between Arg and Phe in the N-terminal end of the B-chain in step b) or iii).

In a further embodiment $X_4$ will comprise at least one Gly to enhance the rate of cleavage by *Achromobacter lyticus* protease in step i) wherein the single-chain insulin precursor is opened.

In a still further embodiment of the present invention $X_2$ and/or $X_4$ have a Glu or Asp as the first amino acid residue seen from the N-terminal end. In this embodiment the peptide chain $X_1$—$X_2$ will comprise a Glu-Glu; a Glu-Asp; an Asp-Asp; or an Asp-Glu-sequence. The same will apply to the. $X_3$—$X_4$-sequence.

In one embodiment of the present invention $X_3$—$X_4$-Arg is selected from the group consisting of Asp-Pro-Arg; Glu-Pro-Arg; and Asp-Glu-Arg and $X_1$—$X_2$-Arg is selected from the group consisting of Asp-Asp-Gly-Asp-Pro-Arg (SEQ ID NO:1) and Glu-Glu-Gly-Glu-Pro-Arg (SEQ ID NO:2).

In another embodiment $X_3$—$X_4$-Arg is selected from the group consisting of Asp-Gly-Arg and Glu-Gly-Arg; and $X_1$—$X_2$-Arg is selected from the group consisting of Asp-Asp-Gly-Asp-Gly-Arg (SEQ ID NO:3) and Glu-Glu-Gly-Glu-Gly-Arg (SEQ ID NO:4).

In a further aspect the present invention is related to single-chain insulin precursors having the formula $$X_1—X_2\text{-Arg-B}(1\text{-}29)\text{-}X_3—X_4\text{-Arg-A}(1\text{-}21)$$

in which $X_1$ is Asp or Glu, $X_2$ is a peptide sequence with 1-10 amino acid residues except Cys, Lys and Arg or is a peptide bond, $X_3$ is Asp or Glu, and $X_4$ is a peptide sequence with 1-10 amino acid residues except Cys, Lys and Arg or is a peptide bond, B(1-29) is the B-chain of human insulin lacking the B30 amino acid residue or an analogue thereof, and A(1-21) is the A-chain of human insulin or en analogue thereof.

Further aspects of the present invention includes polynucleotide sequences encoding the single-chain insulin precursors, vectors containing such polynucleotide sequences and yeast strains transformed with such vectors.

DETAILED DESCRIPTION OF THE INVENTION

Figure 1:
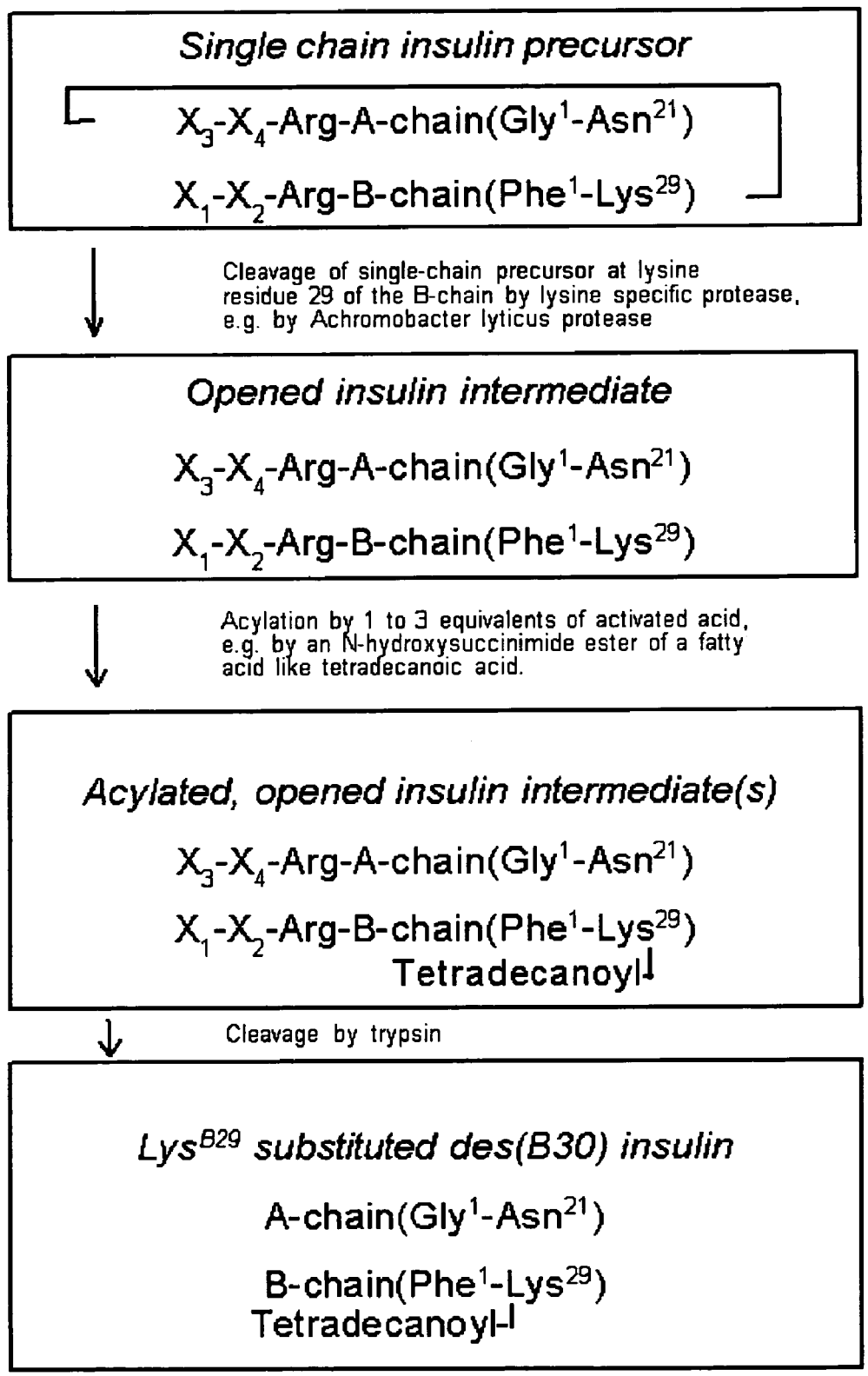
FIG. 1 describes a flow sheet of the process according to the present invention.

The process according to the present invention will be described in further detail in the following. The individual steps are depicted in FIG. 1. The entire process further includes steps of purification, concentration and isolation in the dry state.

We have found that use of selected protective peptide sequences on glycine A1 and phenylalanine B1 in the two chain insulin intermediate enables a nearly quantitative acylation of the epsilon amino group of lysine B29 without using a large excess of the reagent, typically an N-hydroxysuccinimide ester of a fatty acid such as tetradecanoic acid. Both selected peptide sequences have either aspartic acid or glutamic acid residues as their free N-terminals, and arginine residues as their C-terminals where they are connected to the insulin B and A chain, respectively. The number of the amino acid residues in the protecting amino acid sequences range from about 2 to about 10.

Another benefit of the process according to the present invention is that the number of high performance chromatographic purification steps in the down stream purification steps can be markedly reduced. Such chromatographic steps apply expensive gels in the columns an in addition a certain loss of intermediates and final products may be lost in the column and during the subsequent isolation steps.

Another advantage by using the claimed single-chain precursors is that the amount of O-glycosylated biproducts formed during fermentation, i.e. mannosylation in position 8 of the A-chain, may be remarkably lowered, for example to less than about 1%. The removal of such O-glycosylated products by chromatographic processes is associated with loss of product.

In step i) the single-chain insulin precursor is cleaved between B29 lysine and the glutamic or aspartic acid residue constituting the N-terminal amino acid residue in the peptide sequence connecting B29 with A1. The single-chain insulin precursor is hereby opened rendering a two-chain insulin intermediate in which both N-terminals (the $X_1$—$X_2$ Arg and the $X_3$—$X_4$—Arg, respectively) are acidic amino acids. Proteases which cleave specifically at the carbonyl carbon of lysine are well known, in particular the lysine specific protease of *Achromobacter lyticus*. The reaction can be carried out in aqueous solution or in mixtures of organic solvents and water. The reaction rate is at a maximum at a pH of about 9 to 10, but neither pH nor temperature is critical for the specificity of the hydrolysis. The advantage of having glutamic acid or aspartic acid as the N-terminals of the A- and B-chains in the opened precursor in step a) or ii) is that peptide bond formation between $Lys^{B29}$ and any of the N-terminals in the opened molecule is completely abolished. Such peptide bond formation leading to either the original single-chain insulin precursor or a $Lys^{B29}$-$X_1$—$X_2$-Arg-B(1-29) ring, not only leads to direct loss of insulin product but requires additional chromatographic purification steps to separate the undesired biproducts.

The opened two chain insulin intermediate may be purified by suitable chromatographic means and is then isolated by suitable means, e.g. by isoelectric precipitation or by crystallization, before the subsequent step a) or ii).

In step a) or ii) the insulin intermediate is acylated preferentially in the epsilon amino group of $Lys^{B29}$. The optimal conditions for the reaction is in mixtures of organic solvent and water at an apparent pH of about 10 when measured by a glass electrode. The organic solvent is any solvent mixable with water such as dimethylformamide (DMF), dimethylacetamide (DMAC), dioxan, N-methylpyrrolidone (NMP), acetonitrile, ethanol, methanol, isopropanol, tert.-butanol and tetrahydrofuran. The organic solvent facilitates the dissolution of the reagent which is typically an active ester of a long-chain fatty acid. The high pH is required to deprotonate the ε-amino group of $Lys^{B29}$ into the active, free amino group. The pK of this amino group is about 9.6. The preferred activation of the acid to be substituted into insulin is the N-hydroxysuccinimide ester. Such ester shows relatively good solubility in mixtures of water and organic solvents, and the rate of undesired sapofinication (i.e. hydrolysis of ester bond) as compared to the rate of the desired acylation is relatively low compared to other esters, even in the pH range from 9.5 to 10.5. The amount of reagent relative to insulin intermediate is from about 1 to about 3 on a molar basis, but the ratio is not critical. Even when using 3 equivalents of N-hydroxysuccinimide ester at pH 10.2-10.4 the major peak is B29 monoacylated insulin and no starting material is left. When the acylation of B29 lysine is complete, usually within 30 min, the reaction may be stopped by addition of an amine, such as ethanolamine, or ammonia. The benefit of using an amount of the acylating reagent within the above range is primarily that loss of the desired product, the acylated insulin, is minimized because co-precipitation of the acylated insulin with hydrolysed excess of acylating agent is avoided or minimized.

Another advantage of having acidic amino acids, i.e. either glutamic acid or aspartic acid, as the N-terminals of the A- and B-chains in the opened insulin precursor in the acylation reaction is that these amino acids are less prone to be acylated than other α-amino acid residues in N-terminal positions under the conditions required to acylate the ε-amino group of $Lys^{B29}$ enabling use of limited excess of acylation reagent relative to the insulin intermediate to secure quantitative conversion. However, the by-products resulting from acylation of one or both of the N-terminal amino groups in addition to the desired acylation of $Lys^{B29}$ will be converted to the desired product in the third step.

In step b) or iii) the two N-terminal protecting peptide sequences, which may be acylated, are cleaved off from the acylated insulin intermediate by trypsin or a trypsin like protease resulting in the desired desB30 insulin being mono acylated in the ε-amino group in $Lys^{B29}$ and with glycine residue in position A1 and phenylalanine residue in position B1.

The pH in step a) or ii) is between about 9,4 to about 9,8. Good results are obtained at a pH of about 9.6. The temperature in this step is low, around 4° C.

The two-chain insulin intermediate with the selected N-terminal extension on the B-chain and the selected C-terminal extension on the A-chain may be produced by cleavage of a single-chain insulin precursors with the corresponding N-terminal extension on the B-chain and the corresponding connecting peptide between $Lys^{B29}$ and $Gly^{A1}$. Such single-chain insulin precursors may be produced by continuous fermentation in e.g. yeast or *E. coli*. Production of insulin precursors of the type used in the process according to the present invention can be done by a method similar to that disclosed in e.g. U.S. Pat. No. 6,500,645. According to such process, the insulin precursor in question is expressed and secreted from the yeast cells and isolated and purified by a number of well known purification and separation steps.

The first step after fermentation is a centrifugation removing the yeast cells. The single-chain precursors may then be recovered by binding to a cation exchange resin at a pH value below its isoelectric point, and eluted from the cation exchange resin at a pH above its isoelectric pH. The isoelectric pH's of the claimed precursors are typically in the range of 4.5 to 5.5, and binding may be effected from aqueous solution at pH about 3 and elution with a mixtures of water and ethanol at about pH 6. The released single-chain precursor may be precipitated from 17% ethanol at its isoelectric pH. The purity at this stage is typically 85%.

The opening of the single-chain precursor yielding the opened two-chain insulin intermediate may be carried out in a concentrated aqueous solution, e.g. 5-10% w/v, at pH about 10 using a pH stat, optionally in the presence of a buffer such a glutamate or triethylamine. The amount of lysine specific protease applied is about 0.1-0.5% (w/w) of the precursor, and the hydrolysis is completed after about 5 h at room temperature.

The solution is applied to a reverse phase HPLC column ($C_{18}$) and eluted with a gradient in ethanol. This column removes any unopened precursor, the lysine specific protease and a variety of impurities present in small amount, e.g. O-glycosylated derivatives from the fermentation. The presence of $Ca^{2+}$-ions facilitates the separation of O-glycosylated derivatives from the product, i.e. the opened two-chain insulin intermediate, see U.S. Pat. No. 6,180,757.

The insulin intermediate is then isolated by isoelectric precipitation from 17% ethanol. Alternatively, the intermediate can be precipitated by 1-2 M sodium chloride in microcrystalline form in the presence of about 10% ethanol in the pH range from 2 to 3.5. The purity of the opened two-chain insulin intermediate product is about 95-99%.

The opened insulin intermediate is dissolved in water/acetonitrile (1/1 v/v) in a concentration of 8% (w/v) and the pH adjusted to 9.5-10.5 by addition of triethylamine. To this solution is added 1-3 equivalents of tetradecanoic acid N-hydroxysuccinimide ester dissolved in the same volume of acetonitrile. The reaction is allowed to run for 30 min at room temperature keeping the pH about 10 by addition of triethylamine. Any remaining excess of tetradecanoic acid N-hydroxysuccinimide ester is quenched by addition of 10 equivalents of ethanolamine.

HPLC analysis of the reaction mixture shows a major peak of the B29 mono-acylated form and minor peaks of two di-acylated derivatives being substituted in position B29, and of the tri-acylated derivative. Using excess of the reagent gives rise to some tri-acylated derivative. Practically nothing is left of the starting material, the opened two-chain insulin intermediate To this reaction mixture is added 0.5% (w/w relative to opened two-chain insulin intermediate) of porcine trypsin dissolved in water in a volume amounting to about 20% v/v of that of the reaction mixture. After 1 hour at room temperature the conversion to $Lys^{B29}$(tetradecanoyl), des(B30) insulin is complete. Purity by RP-HPLC is about 90%.

The reaction mixture is applied directly to an anion exchange chromatographic column and eluted with a gradient in an acetate salt at pH 7.5 in 42.5% ethanol (v/v) in water. Purity by RP-HPLC is over 99%.

The product in the main peak is recovered by crystallization after addition of 1.5 volumes of aqueous 1 mM $Zn(OAc)_2$, 5 mM trisodium citrate, 0.06% phenol w/v, at a pH of about 7 to 8. The crystallisation is allowed to progress for 24 h at room temperature and for another 24 h at 4° C.

Definitions

By "connecting peptide" or "C-peptide" is meant the connection moiety "C" of the BC-A polypeptide sequence of a single-chain insulin precursor molecule. Specifically, in the natural insulin chain, the C-peptide connects position 30 of the B chain and position 1 of the A chain. In the present insulin precursors the "C-peptide" or "connecting peptide" connects B29 to A1 and differ in sequence and length from that of the natural C-peptide.

With "desB30" or "B(1-29)" is meant a natural insulin B chain or an analogue thereof lacking the B30 amino acid residue and "A(1-21)" means the natural insulin A chain or an analogue thereof. The C-peptide and its amino acid sequence are indicated in the three letter amino acid code.

With "B1", "A1" etc. is meant the amino acid residue in position 1 in the B chain of insulin (counted from the N-terminal end) and the amino acid residue in position 1 in the A chain of insulin (counted from the N-terminal end), respectively. The amino acid residue in a specific position may also be denoted as e.g. $Phe^{B1}$ which means that the amino acid residue in position B1 is a phenylalanine residue.

With "preferential" or "selective acylation" is meant an acylation which occurs in a desired position at a higher degree, preferably at least at two or three times higher degree than in a not desired position. In the method according to the present invention acylation should preferably only take place in the ε-amino group in the $Lys^{B29}$ and not in the two N-terminal α-amino groups at the two chain insulin precursor.

With "insulin precursor" is meant a single-chain polypeptide which by one or more subsequent chemical and/or enzymatic processes can be converted into human insulin or desB30 human insulin. The insulin precursors will have correctly positioned disulfide bridges as in human insulin that is disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$.

A "single-chain" polypeptide is an uninterrupted polypeptide chain of amino acid residues connected by peptide bonds with one N-terminal amino acid residue and one C-terminal amino acid residue and with the disulfide bridges as in human insulin that is between $Cys^{A7}$ and $Cys^{B7}$ and between $Cys^{A20}$ and $Cys^{B19}$ and an internal disulfide bridge between $Cys^{A6}$ and $Cys^{A11}$.

With "Insulin" as used herein is meant human insulin with disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$, porcine insulin and bovine insulin.

By "insulin analogue" as used herein is meant a polypeptide which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues.

The insulin analogues may be such wherein position 28 of the B chain may be modified from the natural Pro residue to Asp, Lys, or Ile. Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin, insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Further insulin analogues are such wherein. One or more of B26-B30 have been deleted. If one or more of the amino acid residues in the positions B26-B30 have been deleted the C-terminal amino acid residue of the B-chain will Lys.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or to an amide group. Other derivatives are obtained by acylating a free amino group or a hydroxy group.

The expression "a codable amino acid residue" is used to indicate an amino acid or amino acid residue which can be coded for by a triplet ("codon") of nucleotides.

In the present context the three-letter or one-letter indications of the amino acids have been used in their conventional meaning as indicated the following table. Unless indicated explicitly, the amino acids mentioned herein are L-amino acids. Further, the left and right ends of an amino acid sequence of a peptide are, respectively, the N- and C-termini unless otherwise specified.

Abbreviations for Amino Acids

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

With "activated acid" is meant a carboxylic acid in which an activated leaving group has been attached to the acyl carbon enabling reaction with an amino group under formation of a peptide bond and release of the leaving group. Activated fatty acids may be activated esters of fatty acids, activated amides of fatty acids and anhydrides or chlorides. Activated fatty acid includes derivatives thereof such as hydroxybenzotriazide and N-hydroxysuccinimide.

With "fatty acid" is meant a linear or branched carboxylic acids having at least 2 carbon atoms and being saturated or unsaturated. Examples of fatty acids are capric acid, lauric acid, tetradecanoic acid (myristic acid), pentadecanoic acid, palmitic acid, heptadecanoic acid, and stearic acid.

With "activated leaving group" is meant a group that activates the acyl carbon of the activated acid for a nucleophil reaction, e.g. by drawing an electron partially away from the carbon, and then leaves the carbon during or after the bonding to the nucleophile, i.e. the amine group. Examples of activating leaving groups are ester groups, amides including azoles and chlorides With "organic solvent" is meant any organic solvent that is mixable with water such as, dimethylformamide, dimethylacetamide, dioxan, N-methylpyrrolidone, acetonitrile, ethanol, methanol, isopropanol, tert.-butanol and tetrahydrofuran.

With "trypsin or a trypsine like enzyme" is meant an endopeptidase that cleaves specifically at lysine and arginine residues. Enzymes that facilitate this hydrolysis are porcine and bovine trypsin.

With "lysine specific protease" is meant an endopeptidase that cleaves specifically at lysine residues but not at arginine residues, such as *Achromobacter lyticus* protease.

"POT" is the *Schizosaccharomyces pombe* triose phosphate isomerase gene, and "TPI1" is the *S. cerevisiae* triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of the invention including yeast aspartic protease 3 (YAP3) signal peptide or any functional analog (Egel-Mitani et al. (1990) YEAST 6:127-137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143-180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analog thereof.

The polynucleotide sequence of the invention may be prepared synthetically by established standard methods, e.g. the phosphoamidite method described by Beaucage et al. (1981) Tetrahedron Letters 22:1859-1869, or the method described by Matthes et al. (1984) EMBO Journal 3:801-805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequence of the invention may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or host cell and which carries a polynucleotide sequence encoding the insulin precursors of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector according to the invention should be capable of replicating in yeast. Examples of sequences which enable the vector to replicate in yeast are the yeast plasmid 2 μm replication genes REP 1-3 and origin of replication.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrg (orotidine-5'-phosphate decarboxylase) and trpC (anthranilate synthase. Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419-434).

The procedures used to ligate the polynucleotide sequence of the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin precursors of the invention, and subsequently inserting this fragment into a suitable expression vector, or by sequentially inserting DNA fragments containing genetic information for the individual elements (such as the signal, pro-peptide, mini C-peptide, A and B chains) followed by ligation.

The present invention also relates to recombinant host cells comprising a polynucleotide sequence encoding the insulin precursors of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In a preferred embodiment, the host cell is a yeast cell. The yeast organism used in the process of the invention may be any suitable yeast organism which, on cultivation, produces large amounts of the insulin precursor of the invention. Examples of suitable yeast organisms are strains selected from the yeast species *Saccharomyces cerevisiae*, *Saccharomyces kluyveri*, *Schizosaccharomyces pombe*, *Sacchoromyces uvarum*, *Kluyveromyces lactis*, *Hansenula polymorpha*, *Pichia pastoris*, *Pichia methanolica*, *Pichia kluyveri*, *Yarrowia lipolytica*, *Candida* sp., *Candida utilis*, *Candida cacaoi*, *Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted insulin precursor of the invention, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

Protracted insulin compositions are well known in the art. Thus, one main type of protracted insulin compositions comprises injectable aqueous suspensions of insulin crystals or amorphous insulin. In these compositions, the insulin compounds utilized typically are protamine insulin, zinc insulin or protamine zinc insulin.

Soluble protracted insulin preparations comprising LysB29-(tetradecanoyl), des(B30) human insulin is known in the clinic as insulin detemir or insulin Levemir®, and from WO 95/07931.

The present invention is described in further detail in the following examples which are not in any way intended to limit the scope of the invention as claimed. The attached FIG. is meant to be considered as integral parts of the specification and description of the invention. All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Fermentation, General Procedure

All expressions plasmids are of the C-POT type, similar to those described in EP 171, 142, which are characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/100075) as are all sequences except the sequence of the EcoRI-XbaI fragment encoding the fusion protein of the leader and the insulin precursor product. In order to express different fusion proteins, the EcoRI-XbaI fragment of pKFN1003 is simply replaced by an EcoRI-XbaI fragment encoding the leader-insulin precursor-fusion of interest. Such EcoRI-XbaI fragments may be synthesized using synthetic oligonucleotides and PCR according to standard techniques.

Yeast transformants were prepared by transformation of the host strain *S. cerevisiae* strain MT663 (MA Ta/MATα pep4-3/pep4-3 HIS4/his4 tpi::LEU2/tpi::LEU2 Cir+). The yeast strain MT663 was deposited in the Deutsche Sammlung von Mikroorganismen und Zelikulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) *Methods in Yeast Genetics*, Cold Spring Harbor Laboratory) containing 1.2 M sorbitol plus 2.5% agar) at 52° C. was added and the suspension poured on top of plates containing the same agar-solidified, sorbitol containing medium.

*S. cerevisiae* strain MT663 transformed with expression plasmids was grown in YPD for 72 h at 30° C. Quantitation of the insulin-precursor yield in the culture supernatants was performed by reverse-phase HPLC analysis with human insulin as an external standard (Snel & Damgaard (1988) Proinsulin heterogenity in pigs. Horm. Metabol. Res. 20:476-488).

Another suitable yeast strain is the strain ME1719 which is a diploid strain and has a phenotype which lacks two aspartyl protease activities, i.e. YPS1 (previously called YAP3) which cleaves C-terminal side of mono- or dibasic amino acid residues (Egel-Mitani, et al., YEAST 6: 127-137, 1990) and PEP4 a vacuolar protease A responsible for activation of other proteases such as protease B, carboxypeptidase Y, aminopeptidase 1, RNase, alkaline phosphatase, acid threhalase and exopolyphosphatase. Moreover the triose phosphate isomerase gene (TPI) has been disrupted which phenotype makes it possible to utilize glucose in transformants grown on glucose containing medium. The genetic background of ME1719 is MATa/α Δyps1::ura3/Δyps1::URA3 pep4-3/pep4-3 Δtpi::LEU2/Δtpi::LEU2 leu2/leu2 Δura3/Δura3. This strain is disclosed in e.g. EP No. 909,312.

Example 2

Expression of Insulin Precursors

Synthetic genes encoding fusion proteins, consisting of the insulin precursor associated with a leader sequence consisting of a pre-peptide (signal peptide) and a pro-peptide, were constructed using PCR under standard conditions (Sambrook et al. (1989) Molecular Cloning, Cold Spring Harbor Laboratory Press) and E.H.F. polymerase (Boehringer Mannheim GmbH, Sandhoefer Strasse 116, Mannheim, Germany). The resulting DNA fragments were isolated and digested with endonucleases and purified using the Gene Clean kit (Bio101 Inc., La Jolla, Calif., USA). Standard methods were used for DNA ligation and transformation of *E. coli* cells were performed by the CaCl$_2$ method (Sambrook et al. (1989) supra). Plasmids were purified from transformed *E. coli* cells using QIAGEN columns (QIAGEN, Hilden, Germany). Nucleotide sequences were determined using the ALF Pharmacia Biotech DNA sequencing system with purified double-stranded plasmid DNA as template. Oligonucleotide primers for PCR were obtained from DNA technology (Arhus, Denmark).

Secretion of the insulin precursor was facilitated by the TA57 leader or the TA39 leader (Kjeldsen et al., 1998. *Protein Expression Purif.* 14, 309-316), although a variety of known yeast leader sequences may be used.

The expression plasmid comprises DNA encoding the insulin precursor in question fused in reading frame with DNA encoding a suitable signal-leader sequence and the TPI-promoter sequence. The plasmid is based on the *S. cerevisiae-E. coli* shuttle POT plasmid (U.S. Pat. No. 5,871,957).

The insulin precursors were secreted as a single-chain N-terminally extended insulin precursor with the selected peptide sequence connecting Lys$^{B29}$ and Gly$^{A1}$.

The following single-chain insulin precursors have been produced:

TABLE 1

| Leader | N-terminal extension on B1 | C-peptide connecting B29 with A1 | Yield in percent of standard (mg/ml) |
|---|---|---|---|
| Alpha | No extension (standard) | AAK | 100 |
| TA57 | EEGEPR (SEQ ID NO:2) | EPR | 389 |
| Alpha | EEGEPR (SEQ ID NO:2) | EPR | 389 |
| TA39 | EEGEPR (SEQ ID NO:2) | EPR | 505 |
| TA57 | DDGDPR (SEQ ID NO:1) | DPR | 473 |

TABLE 1-continued

| Leader | N-terminal extension on B1 | C-peptide connecting B29 with A1 | Yield in percent of standard (mg/ml) |
|---|---|---|---|
| Alpha | DDGDPR (SEQ ID NO:1) | DPR | 446 |
| TA39 | DDGDPR (SEQ ID NO:1) | DPR | 484 |
| TA57 | DDGDPR (SEQ ID NO:1) | DER | 402 |
| Alpha | DDGDPR (SEQ ID NO:1) | DER | 382 |
| TA39 | DDGDPR (SEQ ID NO:1) | DER | 548 |
| TA39 | DDGDPR (SEQ ID NO:1) | DGR | 270 |
| Alpha | DDGDGR (SEQ ID NO:3) | DGR | 360 |

Example 3

Production of Acylated Insulin 1 g of the single chain insulin precursor EEGEPR(SEQ ID NO:2)-B(1-29)-EPR-A(1-21), Mw 6768, was dispersed in 10 ml water and dissolved by addition of NaOH to a pH of 9.7. To the solution was added 5 mg of *Achromobacter lyticus* protease dissolved in 1 ml of water. During the hydrolysis the pH was kept constant between 9:7 and 10.0 by addition of 0.1 M NaOH.

After 5 hours at room temperature less than 1% of the single-chain precursor was left, and the content of the opened two-chain insulin intermediate was 93% as monitored by HPLC.

Mass analysis by MALDI-TOF showed 6786, theory 6786.

The solution was applied directly to a $C_{18}$-substituted silica RP-HPLC column and eluted with a gradient in ethanol from 25 to 33% (v/v) using a total volume of 12 column volumes and a solvent comprising 0.2 M KCl, 0.02 M $CaCl_2$, 0.01 M triethanolamine, the pH adjusted to 7.4 by addition of HCl.

The opened two-chain insulin intermediate emerged after about 6 column volumes. The purity in the top fraction was 99%. The product was isolated by centrifugation after precipitation at pH 5.0 by addition of 1 volume of water to the pooled fractions and cooling to 4° C. Yield 0.8 g.

0.8 g (0.118 mmol) of the opened two-chain insulin intermediate EEGEPR(SEQ ID NO:2)-B(1-29), EPR-A(1-21), purity 96%, was dissolved in 10 ml of a 1:1 mixture (v/v) of water and acetonitrile. The pH was adjusted to 10.4 by addition of triethylamine. The pH was monitored using a glass electrode.

To the solution was added 115 mg of tetradecanoic acid N-hydroxysuccinimide ester (0.354 mmol). The pH dropped to 10.2 during 30 minutes at room temperature.

The reaction was stopped by addition of 0.05 ml ethanolamine.

HPLC of the reaction mixture showed the following relative distribution of compounds:

| | |
|---|---|
| Non-substituted intermediate insulin | 0.0% |
| (A + B) N-terminals mono-acylated derivatives | 6.0% |
| B29 mono-acylated derivative | 86.6% |
| (A, B) N-terminals di-acylated derivative | 0.0% |
| ((A + B) N-terminals, B29) di-acylated derivatives | 4.9% |
| Triacylated derivative | 2.5% |

In this mixture the compounds featuring the B29 substitution amounts to 94%.

3 mg of porcine trypsin dissolved in 3 ml of an aqueous solution was added to the reaction mixture. The pH dropped to 9.8 during 45 min at room temperature.

Analytical RP-HPLC at neutral pH showed 80% of Lys ($N^\epsilon$-tetradecanoyl), des(B30) insulin (MALDI-TOF 5917) eluting in a position after the B29 mono-substituted insulin intermediate and before all three di-substituted insulin intermediates. Des(B30) insulin (MALDI-TOF 5707) eluting early amounted to 1.7%.

The by-product of trypsin cleavage arising from cleavage between arginine B22 and glycine B23 was not detected.

The solution was applied to a column packed with Source 30Q anion exchange resin and eluted with a buffer comprising 42.5% (v/v) of ethanol, 0.02 M Tris buffer pH 7.5, and using a linear gradient of ammonium acetate from 0.03 M to 0.16 M. Lys($N^\epsilon$-tetradecanoyl), des(B30) insulin eluted near the end of the gradient. To the 100 ml pool of the top fractions was added 150 ml of an aqueous solution comprising 0.02 M ammonia, 0.06% (w/v) of phenol and 1 mM zinc acetate during 1 hour. The pH was adjusted to 8.0 and the precipitation was allowed to proceed at room temperature for 18 hours followed by 18 hours at 4° C. The product was harvested by centrifugation, washed with cold water and dried. Yield 0.5 g or 50% over all 3 steps. Purity was estimated to 99.5%.

Mass: MALDI-TOF 5917; theory 5917.

Example 4

Acylation Reactions, Varying the Excess of Reagent and Type of Solvent.

To 4 samples of 0.9 ml of a 8 mM solution of the opened insulin precursor EEGEPR(SEQ ID NO:2)-B(1-29)-EPR-A (1-21) was added 1 N $Na_2CO_3$ to pH 10.0. To these was added 0.9 ml of respectively:

A: a 10 mM solution of tetradecanoic acid N-hydroxysuccinimide ester in acetonitrile B: a 20 mM suspension of tetradecanoic acid N-hydroxysuccinimide ester in acetonitrile C: a 30 mM suspension of tetradecanoic acid N-hydroxysuccinimide ester in acetonitrile D: a 30 mM solution of tetradecanoic acid N-hydroxysuccinimide ester in acetone The excess of acylation reagent becomes 1.25, 2.5, 3.75 and 3.75, respectively.

The apparent pH, as measured by a glass electrode, rose to about 10.6 in the 4 mixtures. After 60 min at room temperature the apparent pH values were about 10.2, and the reactions were stopped by addition of 0.05 ml 1 N NH₄Cl, whereby the apparent pH fell to about 10.0. The compositions of the reaction products were analysed by RP-HPLC. The (A or B) N-terminal mono-acylated derivatives were not detectable in any of the 4 samples. The tri-acylated derivative emerged too late to be detected.

To the 4 reaction mixtures was added 1 mg of trypsin dissolved in 1 ml of water. After 60 min at room temperature the reactions were stopped by adjustment of the pH to 2.5. The compositions of the final reaction products were again analysed by RP-HPLC.

The results appear from the following table 2:

TABLE 2

| Product | A, % | B, % | C, % | D, % |
|---|---|---|---|---|
| Mixtures after acylation (excess reagent) | 1.25 | 2.5 | 3.75 | 3.75 |
| Non-substituted intermediate insulin | 23.8 | 11.2 | 5.9 | 4.8 |
| (A, B) N-terminals mono-acylated derivatives | — | — | — | — |
| B 29 mono-acylated | 66.1 | 73.1 | 76.4 | 78.5 |
| (A, B) N-terminals di-acylated derivative | 0.4 | 0.8 | — | 0.7 |
| ((A or B) N-terminal, B29) di-acylated derivative | 3.2 | 7.2 | 8.4 | 8.6 |
| Triacylated derivative | n.d. | n.d. | n.d. | n.d. |
| Mixtures after acylation and cleavage by trypsin | | | | |
| des(B30) human insulin | 21.0 | 10.8 | 4.1 | 5.0 |
| Lys(N$^\varepsilon$-tetradecanoyl), des(B30) insulin | 76.2 | 84.2 | 88.3 | 83.0 |

Example 5

Acylation Reaction using Asparagine as the N-terminal Amino Acids of the Chains and Gly Adjacent to Arg in the C-peptide.

Opened two-chain insulin intermediate DDGDPR (SEQ ID NO:1)-B(1-29)-DGR-A(1-21), Mw 6690, was prepared as a wet precipitate in analogy to the procedure in example 3. A total of 420 mg, equal to 0.063 mmol of the opened insulin intermediate in the form of about 3 ml of wet precipitate, was dissolved in N-methylpyrrolidone to make 10 ml, and the pH adjusted to 9.6 using triethylamine.

To this solution was added 41 mg (2 equivalents) of tetradecanoic acid N-hydroxysuccinimide ester (Mw 325) dissolved in 3 ml of N-methylpyrrolidone, and the acylation reaction was conducted at room temperature, keeping the pH constant at 9.6 by addition of triethylamine. After 60 min the reaction was stopped by the addition of 1.5 ml 1 N NH₄Cl in water, whereby the pH became 9.3.

The composition of the reaction products of the acylation was analysed by RP-HPLC.

To the reaction mixtures was added 2 mg of trypsin dissolved in 26 ml of water. The trypsin digestion was conducted for 2 hours at room temperature and overnight at 4° C.

The composition of the reaction products of the trypsin digestion was analysed by RP-HPLC. The results appear from the following table 3:

TABLE 3

| Product | % |
|---|---|
| Mixture after 60 min of acylation | |
| Non-substituted opened two-chain intermediate | 1.8 |
| (A, B) N-terminals mono-acylated derivatives | 0.8 |
| B 29 mono-acylated | 60.8 |
| (A, B) N-terminals di-acylated derivative | 0.6 |
| ((A or B) N-terminal, B29) di-acylated derivative | 30.6 |
| (A1 and B1) N-terminals and B29 triacylated derivative | 3.7 |
| Mixture after acylation and cleavage by trypsin | |
| des(B30) human insulin | 1.8 |
| Lys(N$^\varepsilon$-tetradecanoyl), des(B30) insulin | 88.1 |
| des(B23-B30) human insulin | 4.3 |

Example 6

Acylation Reaction using Asparagine as the N-terminal Amino Acids of the Chains and Glycine Residues Adjacent to Arginines in the C-peptide and in the B-chain Extension.

Opened two-chain insulin intermediate DDGDGR(SEQ ID NO:3)-B(1-29)-DGR-A(1-21), Mw 6649, is prepared as a wet precipitate in analogy to the procedure in example 3. A total of 665 mg, equal to 0.1 mmol of the opened two-chain intermediate in the form of about 3 ml of wet precipitate, is dissolved in N-methylpyrrolidone to make 1.0 ml, and the pH is adjusted to 9.6 using triethylamine.

To this solution is added 68 mg (3 equivalents) of tetradecanoic acid N-hydroxysuccinimide ester (Mw 325) dissolved in 3 ml of N-methylpyrrolidone, and the acylation reaction is conducted at room temperature, keeping the pH constant at 9.6 by addition of triethylamine. After 60 min the reaction is stopped by the addition of 2 ml 1 N NH4Cl in water, and the pH was readjusted to 9.6.

The composition of the reaction products of the acylation is analysed by RP-HPLC.

To the reaction mixtures is added 2 mg of trypsin dissolved in 60 ml of water, reducing the concentration of organic solvent to about 14%.

The trypsin digestion is conducted for 24 hours at 4° C.

The composition of the reaction products of the trypsin digestion is analysed by RP-HPLC.

The invention claimed is:

1. A method for making an acylated insulin or an insulin analogue, said method comprising:

a) acylating an insulin intermediate with an acylating agent in a solvent, wherein said insulin intermediate has the formula:

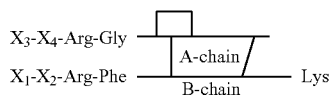

wherein the $X_3$—$X_4$ sequence is selected from the group of sequences consisting of Asp-Pro, Glu-Pro, Asp-Glu, Asp-Gly and Glu-Gly; and the $X_1$—$X_2$ sequence is selected from the group of sequences consisting of Asp-Asp-Gly-Asp-Pro (amino acids 1-5 of SEQ ID NO:1), Glu-Glu-Gly-Glu-Pro (amino acids 1-5 of SEQ ID NO:2), Asp-Asp-Gly-Asp-Gly (amino acids 1-5 of SEQ ID NO:3) and Glu-Glu-Gly-Glu-Gly (amino acids 1-5 of SEQ ID NO:4), B-chain is the B-chain of human insulin or an analogue thereof, and A-chain is the A-chain of human insulin or an analogue thereof, at the C-terminal lysine amino group in the B-chain, and b) cleaving the peptide bond between Arg and B1 and between Arg and A1 in the acylated intermediate by trypsin or a trypsin like protease to produce an acylated insulin or insulin analogue.

2. The method according to claim 1, wherein the insulin intermediate in step a) is produced by cleavage of a single-chain insulin precursor having the formula:

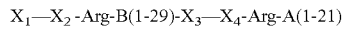

wherein the $X_3$—$X_4$ sequence is selected from the group of sequences consisting of Asp-Pro, Glu-Pro, Asp-Glu, Asp-Gly and Glu-Gly; and the $X_1$—$X_2$ sequence is selected from the group of sequences consisting of Asp-Asp-Gly-Asp-Pro (amino acids 1-5 of SEQ ID NO:1), Glu-Glu-Gly-Glu-Pro (amino acids 1-5 of SEQ ID NO:2), Asp-Asp-Gly-Asp-Gly (amino acids 1-5 of SEQ ID NO:3) and Glu-Glu-Gly-Glu-Gly (amino acids 1-5 of SEQ ID NO:4), B(1-29) is the B-chain of human insulin lacking the B30 amino acid residue or an analogue thereof, and A(1-21) is the A-chain of human insulin or an analogue thereof, with a lysine specific protease that cleaves the peptide bond between $Lys^{B29}$ and $X_3$.

3. The method according to claim 1 further comprising the step of isolating the acylated insulin or insulin analogue produced in b).

4. The method according to claim 1, wherein the acylating agent in step a) is used in an amount of 1 to 5 equivalents.

5. The method according to claim 1, wherein the acylating agent in step a) is an activated ester or an activated amide of a fatty acid.

6. The method according to claim 5, wherein the activated fatty acid ester is an N-hydroxysuccinimide ester of a fatty acid.

7. The method according to claim 1, wherein the lysine specific protease is *Achromobacter lyticus* protease.

8. The method according to claim 1, wherein the pH in step a) is between about 9 and about 10.5.

9. The method according to claim 8, wherein pH in step b) is between about 9.3 and 9.9.

10. The method according to claim 5, wherein the fatty acid is a long chain fatty acid having from 6 to 18 C-atoms.

11. The method according to claim 10, wherein the fatty acid has from 10 to 18 C-atoms or from 10 to 14 C-atoms.

12. The method according to claim 11, wherein the fatty acid is selected from the group consisting of capric acid, lauric acid, tetradecanoic acid (myristic acid), pentadecanoic acid, palmitic acid, heptadecanoic acid, and stearic acid.

13. The method according to claim 1, wherein the solvent in step a) is a mixture of water and a water mixable organic solvent selected from the group consisting of N-methylpyrrolidone (NMP), dimethylformamide (DMF), dimethylacetamide (DMAC), acetonitrile, tetrahydrofuran, dioxan, methanol, ethanol, isopropanol and tert-butanol.

14. The method according to claim 1, wherein $X_2$ comprises at least one Gly.

15. The method according to claim 1, wherein $X_4$ comprises at least one Gly.

16. The method according to claim 1, wherein $X_4$ is Gly.

* * * * *